(12) United States Patent
Rothweiler et al.

(10) Patent No.: US 10,398,496 B2
(45) Date of Patent: Sep. 3, 2019

(54) ELECTROSURGICAL INSTRUMENT WITH CLAMPING PRESSURE CONTROL FOR ELECTRODE BRANCHES

(71) Applicant: Aesculap AG, Tuttlingen (DE)

(72) Inventors: Christoph Rothweiler, Donaueschingen (DE); Nikolaus Hafner, Tuttlingen (DE); Eugen Herner, Balingen (DE); Patrick Heizmann, Hüfingen (DE)

(73) Assignee: Aesculap AG (DE)

( * ) Notice: Subject to any disclaimer, the term of this patent is extended or adjusted under 35 U.S.C. 154(b) by 468 days.

(21) Appl. No.: 14/440,647

(22) PCT Filed: Oct. 30, 2013

(86) PCT No.: PCT/EP2013/072721
§ 371 (c)(1),
(2) Date: May 5, 2015

(87) PCT Pub. No.: WO2014/072215
PCT Pub. Date: May 15, 2014

(65) Prior Publication Data
US 2015/0282866 A1    Oct. 8, 2015

(30) Foreign Application Priority Data
Nov. 7, 2012 (DE) .................. 10 2012 110 660

(51) Int. Cl.
*A61B 18/14* (2006.01)
*A61B 17/072* (2006.01)
(Continued)

(52) U.S. Cl.
CPC .... *A61B 18/1445* (2013.01); *A61B 17/07207* (2013.01); *A61B 17/1155* (2013.01);
(Continued)

(58) Field of Classification Search
CPC .............................. A61B 17/07207
See application file for complete search history.

(56) References Cited

U.S. PATENT DOCUMENTS

| 5,467,911 A | 11/1995 | Tsuruta |
| 6,626,929 B1 | 9/2003 | Bannerman |

(Continued)

FOREIGN PATENT DOCUMENTS

| CN | 1989912 | 7/2007 |
| CN | 201012103 | 1/2008 |

(Continued)

OTHER PUBLICATIONS

German Search Report for German Application No. 10 2012 110 660.6 dated Aug. 21, 2013, with partial translation T2.

(Continued)

*Primary Examiner* — Carl H Layno
*Assistant Examiner* — Jennifer L Ghand
(74) *Attorney, Agent, or Firm* — RatnerPrestia

(57) ABSTRACT

A surgical instrument in HF design includes two tissue branches, at least one of the tissue branches being movable relative to the other tissue branch and being able to be applied to the other tissue branch with a predetermined or predeterminable contact pressure via an actuation mechanism while clamping body tissue between the tissue branches. A clamping pressure controlling or adjustment device is interconnected in a force or torque gear train between the actuation mechanism and the at least one movable tissue branch.

17 Claims, 8 Drawing Sheets

(51) Int. Cl.
*A61B 17/115* (2006.01)
*A61B 90/00* (2016.01)
*A61B 18/00* (2006.01)

(52) U.S. Cl.
CPC ...... *A61B 90/03* (2016.02); *A61B 2017/0725* (2013.01); *A61B 2018/0063* (2013.01); *A61B 2090/032* (2016.02); *A61B 2090/065* (2016.02); *A61B 2090/0811* (2016.02)

(56) References Cited

U.S. PATENT DOCUMENTS

| | | |
|---|---|---|
| 8,241,284 B2 | 8/2012 | Dycus |
| 2003/0069592 A1 | 4/2003 | Adams |
| 2004/0122423 A1 | 6/2004 | Dycus |
| 2008/0078805 A1 | 4/2008 | Omaits |
| 2009/0230170 A1 | 9/2009 | Milliman |
| 2010/0237132 A1 | 9/2010 | Measamer |
| 2011/0022052 A1 | 1/2011 | Jorgensen |

FOREIGN PATENT DOCUMENTS

| | | |
|---|---|---|
| CN | 101843509 | 9/2010 |
| DE | 60121229 | 5/2007 |
| EP | 1372507 | 6/2006 |
| EP | 1952777 | 8/2008 |
| EP | 2055246 | 5/2009 |
| EP | 1656901 | 9/2009 |
| EP | 2160984 | 3/2010 |
| EP | 2233084 | 9/2010 |
| EP | 2083710 | 7/2014 |
| EP | 2079372 | 12/2014 |
| JP | 2008534069 A | 8/2008 |
| JP | 2010221027 A | 10/2010 |
| WO | 2006104836 A2 | 10/2006 |
| WO | 2008039249 | 4/2008 |
| WO | 2008039250 | 4/2008 |

OTHER PUBLICATIONS

International Search Report for International Application No. PCT/EP2013/072721 dated Mar. 11, 2014.
Chinese Office Action for Chinese Application No. 201380058379.5, dated Oct. 9, 2016 with translation, 20 pages.
Japanese Office Action with English language translation for Application No. 2015-540113, dated Jul. 14, 2017, 9 pages.
Notification of Reasons for Rejection for Japanese Application No. 2015-540113, dated Apr. 17, 2018, including English translation, 11 pages.

ELECTROSURGICAL INSTRUMENT WITH CLAMPING PRESSURE CONTROL FOR ELECTRODE BRANCHES

RELATED APPLICATIONS

This application is the U.S. national stage entry of International Application No. PCT/EP2013/072721, filed Oct. 30, 2013, which claims the benefit of priority of German Application No. DE 10 2012 110 660.6, filed Nov. 7, 2012, the contents of both applications being incorporated by reference herein in their entireties.

FIELD

The present invention relates to an electrosurgical instrument, in particular for laparoscopic operations.

BACKGROUND

Following the surgical removal of a hollow vessel portion, e.g. with an intestinal resection due to a tumor having affected a bowel section, the two hollow vessel portions have to be reconnected at their opened ends in such a manner that a continuous pathway is produced. This is referred to as end-to-end anastomosis. As a standard, the two opened ends are reattached to each other with clip suturing devices.

In particular with operations on the small and large intestines, leaky suture connections (suture insufficiency) occur from time to time, which are associated with a serious progress of disease and a high mortality rate, too.

Traditionally, wounds (for instance with operations) are closed by sewing them with stitches as an alternative to clips. Both techniques are relatively complex and leave foreign matter in the body at least temporarily, which may provoke allergic reactions in some cases. What is more, there is an increased risk of an accidental introduction of foreign matter, in the worst case pathogenic agents or allergens. This is why one tries to replace such methods and/or at least to use them as rarely as possible.

For preparing a surgical anastomosis, i.e. an operatively established connection between blood vessels, nerves or hollow organs as explained above, a novel technique has been developed which is the sealing of tissue with bipolar high-frequency current, the so called "Tissue Fusion Technology" (TFT). This technique does without any foreign matter staying in the body and also sterilizes the tissue during the sealing process, so that the risk of infection can be further reduced.

The tissue fusion by means of high-frequency technology (HF) is based on the denaturation of proteins which are present in many tissues. This allows to weld collagen-containing tissue. During the welding process, the tissue is heated up to temperatures above the protein denaturation temperature, and together with the intra- and extracellular matrix is converted into a gel-like state. After compression of the tissue faces, the liquefied tissue cools down to a fused mass, effecting a reliable connection of the tissue.

For the purpose of welding the hollow vessel portions, the tissue grasped between two clamping jaws is exposed to electrical current which flows between electrodes provided on the two clamping jaws. Any excess tissue which protrudes into the hollow organ is subsequently cut off as in the clip-based technology in order to obtain an undisturbed passage of the hollow organ.

For preventing the sealing or welding from breaking down, the parameters acting on the tissue have to be detected and controlled. In order to ensure this, a precise control of temperature, pressure, tissue impedance, distance and position etc. is required.

It is desirable to realize a uniform treatment of the tissue which is held between the clamping jaws, so that all zones are reliably reached and no zone is exposed to an excessively high current. To this end, it has to be ensured that the HF electrodes are uniformly spaced from each other and aligned so as to be parallel to each other.

The prior art contains clip suturing instruments in which the height of the deformed clips can be adjusted. This technology, however, cannot be directly compared with an adjustment of the surface pressure, as in this way the compression of the tissue is effected merely in indirect fashion on the basis of the difference between the thickness of the tissue and the height of the clips. Thus, the pressure exerted by the clips which have been set cannot be adjusted and can only be estimated in advance on the basis of empirical values with respect to the behavior of the respective tissue. In the course of the surgical operation, the surgeon does not receive any feedback about a possible mechanical damage of the tissue going beyond the damage inevitably occurring during setting the clips.

The following patent applications are known which describe adjustable distances for holding tissues to be stapled for circular clip suturing instruments:

EP2083710A1 discloses a cartridge arrangement for carrying a clip cartridge. The cartridge arrangement can be moved to a shooting position for setting the clips. An anvil on which the clips are set is functionally coupled to an anvil closure. The anvil closure may selectively move the anvil in a proximal direction toward the cartridge arrangement in order to clamp a part of the tissues, to be stapled, by the cartridge arrangement and the anvil. The device may further comprise an actuator which cooperates with the anvil closure in such a manner that the anvil is moved in the proximal direction to increase the clamping effect whereby the tissue is compressed between the cartridge arrangement and the anvil to a greater extent. An element intended for producing a variable load allows to preselect the pressure on the tissue between the anvil closure and the actuator before the clip is set.

EP2055246A1 discloses a surgical clip device for circular anastomoses. The device comprises a display showing the surgeon the approach between anvil and cartridge arrangement and the readiness for setting the clips. The anvil can be tilted away after the setting process in order to be able to remove the device from the hollow organ after the stapling process in an easier way.

Also EP2160984A2 discloses a surgical clip device which is comparable with the device known from EP2055246A1 with regard to the present invention.

In order to avoid tissue damage, pressure limiting means are used in instruments for minimally invasive surgery (MIC instruments).

With coagulation instruments as described here, it is possible to maintain a desired distance between the electrodes by spacers mounted on the clamping jaws. However, if the clamping jaws comprise a larger number of spacers provided thereon, as suggested e.g. in EP 1 656 901 B1, EP1 952 777 A1, EP 1 372 507 A1 or US 2004/122423 A1, it is inevitable that the spacers perforate the tissue to be treated, as the tissue is compressed under the spacers with closed clamping jaws to such an extent that there are permanent damages on the tissue. This has negative effects on the result of the sealing process.

As the spacers are further made from an electrically non-conductive material for avoiding a short-circuit between the HF electrodes, a so-called coagulation shade develops in the vicinity of said spacers, which means that the tissue portions are encapsulated in the vicinity of or under the spacers, hence are not supplied with electrical current or only to an insufficient extent, and an unsatisfactory welding of the vessel portions will occur. Furthermore, it has turned out that electrically insulating spacers of this type may readily flake off, in particular in case they are attached to the electrode e.g. by gluing, with the risk that they may find their way into the patient body possibly even unnoticed. In addition to that, the predefined electrode spacing is not ensured any more.

Therefore, modern clip suturing instruments available on the market comprise an adjustable clip height and a display to see if the "correct" clip height has been set. However, the user is not given any information on how the tissue is compressed during the setting or stapling process or otherwise stressed. This means that the user does not have any feedback about a possible mechanical damaging of the tissue. What is more, the surface pressure during setting the clips does not necessarily have to be directly related to the force exerted by the set clip, because the tissue may change around the clip after connection in particular in the event of complications. It may get swollen or become inflamed, for instance. With coagulation instruments, the adjustment of the distance between the clamping jaws which in functional view correspond to the anvil and the opposite holder (in most cases the clip cassette) of the clip-type instrument, is solved via spacers.

EP2079372A1 is deemed to represent the closest prior art. Specifically, this document discloses an apparatus comprising a cartridge assembly unit for receiving a clip magazine. An anvil is coupled to an anvil closure. The anvil closure is able to selectively move the anvil in the proximal direction toward the cartridge assembly unit to clamp a part of a tissue, to be stapled, between the cartridge assembly unit and the anvil. The device is also capable of limiting a compression of the tissue between the anvil closure and the actuator to prevent a further movement of the anvil in the proximal direction toward the cartridge assembly unit, if the predetermined compression level is reached.

In terms of circular clip suturing instruments, there are also known following documents relating to safety precautions:

US2009230170A1 discloses a surgical clip device comprising a housing, an elongated portion, a distal end piece, and a movable handle which is in a mechanical cooperation with the housing and can be moved between a first, open position and a second position approaching the distal end piece for clamping a tissue. A ratchet mechanism cooperates with the movable handle in mechanical fashion to prevent the movable handle toward the first, open position before the movable handle has reached a predetermined position.

EP2233084A1 shows a surgical clip device comprising an anvil locking system. This prevents an undesired displacement of the anvil in the axial direction.

However, comparable safety precautions in the use of HF sealing instruments are not known. Furthermore, it is not possible to readily transfer the requirements regarding the safety engineering which is due to the completely different ways of connecting the tissue.

SUMMARY

Therefore, it is the object of the invention to provide a sealing instrument which is capable of minimizing the tissue damages in the anastomosis.

This object is achieved by a device/a surgical instrument as described herein.

The present invention mainly relates to the control and adjustability of the surface pressure (tissue clamping pressure or force) which acts on the tissue especially prior to and during the sealing process as well as during the final cutting process. Solutions are presented for a circular, a linear and a laparoscopic sealing instrument. Further, possibilities are shown to improve the controllability of the method by additional safety means.

According to the invention, it has been found that tissue sealings (in contrast to setting clips as discussed in the references explained above) need a defined surface pressure area and a defined surface pressure maintained for a sufficiently long time. This is why it is necessary to provide a corresponding clamping pressure adjustment device on the instruments. This allows to avoid or at least reduce the problems explained above which occur with spacers, as there is no need to use any spacers which may compress/perforate the tissue in part; even with the use of spacers, only a predefined force acts on the tissue, which does not result in damages.

The solution described here shows the first known solution concept for a preferably circular sealing instrument. Moreover, comparable mechanical systems of clip suturing instruments are not known, as they are not needed in this type and in this context, as already explained. Due to the fact that in particular linear and laparoscopic sealing instruments are used for a multitude of tissue types and indications, the invention provides for an adjustment possibility for the user, allowing the ideal surface pressure for each application. All instrument concepts known hitherto do not provide the above mentioned adjustment possibilities, limiting the field of application of these instruments to certain tissue types and indications.

Based on the above-mentioned prior art, the installation of a pressure control or pressure adjusting unit in a surgical instrument preferably for sealing purposes and working with bipolar high-frequency technology allows to achieve a reproducible sealing of the tissue. It is guaranteed that the tissue is held between the two electrodes with a defined contact force. As the electric sealing achieves a more uniform distribution of stresses on wounds, it is possible to create a consistently good tissue bond and the healing process can be accelerated.

According to the invention, the user is able to actively adjust the surface pressure acting on the tissue in a predefined range. In a preferred embodiment, the user can directly control by means of a mechanical display system if the surface pressure is correctly set. An excessive contusion of the tissue is avoided by the defined force effect. In general, the possibility of adjusting the surface pressure expands the field of use of the instruments. This enhances the safety of users and patients.

According to a further embodiment, an additional display at the proximal end, in particular in the case of a circular instrument, is a further assistance for the user, as it happens quite frequently that the area of the display scale is not well visible.

It is particularly preferred that the surface pressure is applied by an adjustable spring mechanism. Springs such as gas pressure springs, helical tension springs, helical compression springs, disc springs or leaf springs are known mechanical or pneumatic elements for exerting forces. These springs are pretensioned, which can be effected by means of a pretensioning screw. In this way, the preselected pretension of the spring, the spring force produced at a defined distance and the surface area of the clamping jaws allow to adjust the surface pressure on the tissue in an easy and reliably reproducible manner.

As an alternative, the force for producing the surface pressure may also be created in some other way. In the case of telesurgical instruments, for instance, which are equipped according to the invention, it is conceivable to adjust the surface pressure through a motor-assisted drive system. Here too, a spring may be provided which either builds up a counter force against a motor force clamping the tissue or is pretensioned in motorized fashion itself.

It is also conceivable to couple an eccentric cam to the clamping jaws in such a manner that the surface pressure can be adjusted by rotating the eccentric cam. Compared to the arrangement made up of a spring and a pretensioning screw as suggested above, the adjustment via an eccentric cam has the advantage that it is more space-saving and can be re-adjusted with a smaller motion amplitude as a rule.

It is particularly advantageous that the entire mechanic adjustment system can be accommodated as a whole. In this way, there are advantages regarding a compact construction and an easier replacement in case of possible defects.

In addition, the instrument according to the invention can be further developed in such a manner that safety mechanisms are provided for ensuring the sealing process without the risk of an inadvertent tissue damage (for instance caused by an incorrectly set surface pressure or an instrument which is not properly inserted).

More specifically, the problem is solved with a surgical instrument preferably in HF design or circular HF design, comprising two tissue or clamping branches (also referred to as instrument head and anvil) which are equipped with electrodes and of which at least one can be moved relative to the other one and is able to be applied to the other tissue branch with a predetermined or predeterminable contact pressure via an actuation mechanism (while clamping body tissue therebetween). According to the invention, a clamping pressure control device or clamping pressure adjustment device (or also a clamping providing device) is provided which is (serially) interconnected in a force or torque gear train between the actuation mechanism and the at least one movable tissue branch.

The clamping pressure adjustment device is adapted to introduce a predetermined or predeterminable force (moment) into the force or torque gear train if there exists a predetermined or predeterminable actuation amount of the actuation mechanism; according to said force, an associated clamping pressure (clamping force) is exerted on the clamped tissue and is also maintained in accordance with the actuation period.

The clamping pressure control or adjustment device preferably comprises an energy accumulator (acting in a stroke-like or linearly displaceable manner) which can be loaded via the actuation mechanism by a defined/definable (displacement) amount or within a defined/definable amount, in which a resulting actuation force or actuation moment transmitted via the force or torque gear train produces the predetermined or predeterminable contact pressure. In other words, it is preferred to implement the control or adjustment device with an energy accumulator (compression spring) which exerts a related force on a downward force transmission path with a specific deformation path such that, if the energy accumulator (the spring) is deformed from outside by means of the actuation mechanism beyond a given extent (spring deflection) and so as to be visible from outside, the resulting deformation force is applied via the force transmission system to the instrument branches as a clamping force.

Thus, the clamping pressure control or adjustment device acts according to the principle of an elastically yielding lifting cylinder whose elastic resilience can be adjusted preferably in the axial direction. This means that the clamping force is not directly transferred via the actuation element but in indirect manner via the energy accumulator as a function of its deformation path as well of its deformation characteristic and hence is reproducible. With this, the present invention explicitly differs from a simple trigger mechanism (overload protection) which is interposed, for instance, between the actuation element and the force transmission system and interrupts the path of force if a preset maximum actuation force is achieved. Such a trigger mechanism would indeed prevent the tissue from being excessively stressed, but it could not ensure that a given clamping force is actually reached and also maintained for a given period of time.

The energy accumulator may be additionally provided with a safety means in the form of a loading amount sensor allowing to activate the surgical instrument for triggering a specific instrument function (e.g. the supply of HF current) unless a specific loading amount is achieved. It is further preferred that the energy accumulator is a (compression) spring or spring arrangement which can be deformed according to the amount. Here, it has turned out to be advantageous if the force or torque gear train optionally comprises at least two mutually movable elements, for instance two push-type elements (axially) movable relative to each other in the manner of a telescope, between which the spring is disposed. Hence, if one of the push-type elements (e.g. the outer one) is axially moved, the other push-type element (e.g. the inner one) is displaced without any relative displacement via the intermediate spring arrangement, as long as there is no resistance against movement applied on the other (inner) push-type element.

As soon as the other (inner) push-type element encounters any resistance and is possibly stopped, there occurs an axial displacement between the two push-type elements, whereby the intermediate spring arrangement is tightened and exerts an axial force on the other (inner) push-type element. The axially acting spring arrangement has turned out to be particularly advantageous (for instance compared to a rotary spring), as it exhibits a substantially linear spring characteristic over a comparably long spring deflection.

In this arrangement, the elements which are movable relative to each other may each be formed with spring seats, of which at least one is preferably adjustable in order to bring about different deformation amounts (and hence different pressure forces) of the spring within a maximum (always constant) actuating travel or actuation amount of the actuation mechanism.

Further, the energy accumulator may be mechanically coupled to a display device via which the loading amount and the deformation amount effected by the actuation mechanism can be detected and preferably visually displayed as a current branch contact pressure. Said display device may be a drive bar or a pointer in operative connection with one of the spring seats (a spring seat facing the actuation mechanism), which is entrained by the spring seat at the beginning of a spring deformation initiated by the actuation mechanism and in this way detects said deformation path and preferably displays it. In addition or alternatively, it is also possible to provide a force or torque limiting means preferably in the form of a sliding clutch, which is arranged between the actuation mechanism and the energy accumulator. As an option, the force or torque limiting means may be adjustable, with the possibility that the adjustment can be displayed also in this case in order to obtain the clamping pressure achievable therefrom.

Finally, it is to be noted that a spring represents only one form of the constructional configuration of the energy accumulator according to the invention. Instead, the energy accumulator may also be realized in the form of other solutions such as an electromagnet, a coil etc., whose magnetic fields are adjustable via the actuation mechanism in order to supply the gear train with a corresponding force or torque.

BRIEF DESCRIPTION OF THE DRAWING FIGURES

The invention is explained in more detail below on the basis of several exemplary embodiments with reference to the accompanying Figures in which.

DETAILED DESCRIPTION

Figure 1:
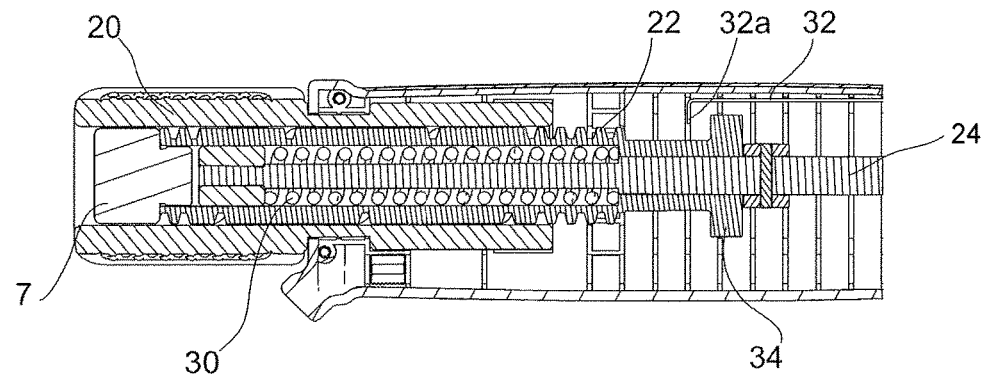
FIG. 1 is a longitudinal sectional view of an exemplary clamping pressure control device (mechanical pressure control means) at the proximal end of a circular electrosurgical instrument according to a first preferred exemplary embodiment of the invention.

Applicant has developed a new design for sealing instruments which offers the user the ability to set a defined surface pressure (clamping pressure) at the clamping jaws/branches of the instrument. The optimum, adjustable range for the treatment result from preferably 0.7 N/mm$^2$ to 2.0 N/mm$^2$ has been defined by preliminary tests and is to be reliably adjustable by clamping pressure control device according to the invention. In this context, it should be pointed out that other values for the preferred clamping pressure are also contemplated depending on the body tissue to be treated.

The clamping pressure control device according to the invention is based on the general idea that e.g. a pretensioning spring, as a simple variant of an energy accumulator having predefined spring characteristics, exerts in the presence of a specific deformation path, a related specific spring force which can be calculated from the spring characteristic and is reproducible again and again. If such a pretensioning spring is deformed over a specific spring path, the elastically deformed spring travel which can be visually read out in simple manner (is readily presentable) allows to draw a conclusion on the spring force which can be produced or is produced in this process, which then can be applied for instance on the instrument clamping jaws/branches for compressing any body tissue clamped therebetween. This in turn allows, basically in consideration of the efficiency of the force/moment gear train from the spring to the clamping jaws/branches, to establish a relation between a specific spring pretensioning force (corresponding to the visually displayable spring deformation path) and a specific surface pressure between the clamping jaws/branches. This means that the current pressure can be precisely represented in indirect manner via the elastic spring deformation path. It goes without saying that the spring is only one variant for an energy accumulator. It is conceivable to provide an electric energy source instead of the mechanical one and to control the currently delivered energy as a function of the actuation amount of an actuation device. Said delivered energy could be transformed into an actuation force in analogy to the spring pretensioning force. In the following, however, reference is made only to a spring as an energy accumulator.

Incidentally, the above-mentioned principle can be applied to all kinds of surgical instruments clamping tissues, irrespective of whether the force for deforming the pretensioning spring can be applied manually or by motor assistance. Further, said functional principle can be expanded at will in terms of safety technology, for instance by interposing a force or torque limiter e.g. in the form of a sliding clutch between the pretensioning spring and the mechanism for pretensioning the spring or by the motor-assisted drive system automatically preventing the overrun of a maximum drive system force, such as a stepper motor or a hydraulic or pneumatic drive comprising a pressure limiting valve.

Figure 5:
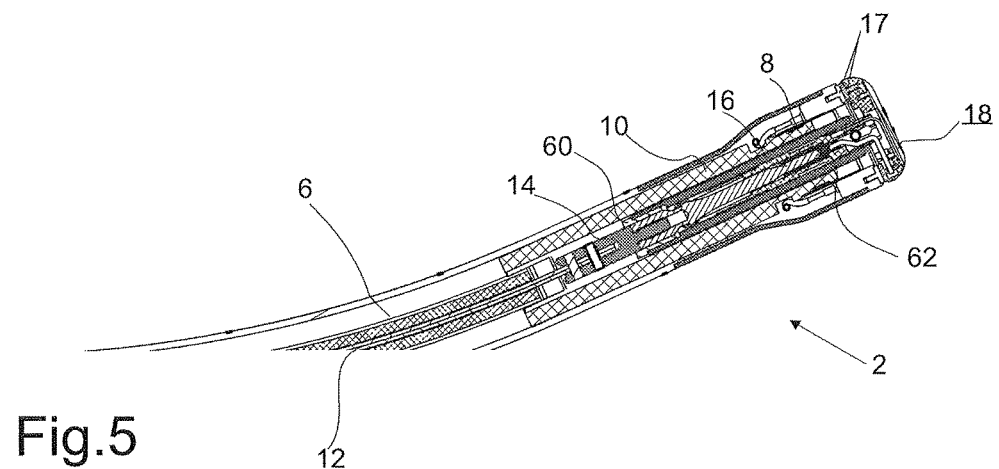
FIG. 5 shows the shaft-/instrument head of the electrosurgical instrument according to the first preferred exemplary embodiment together with its functional elements.
Figure 6:
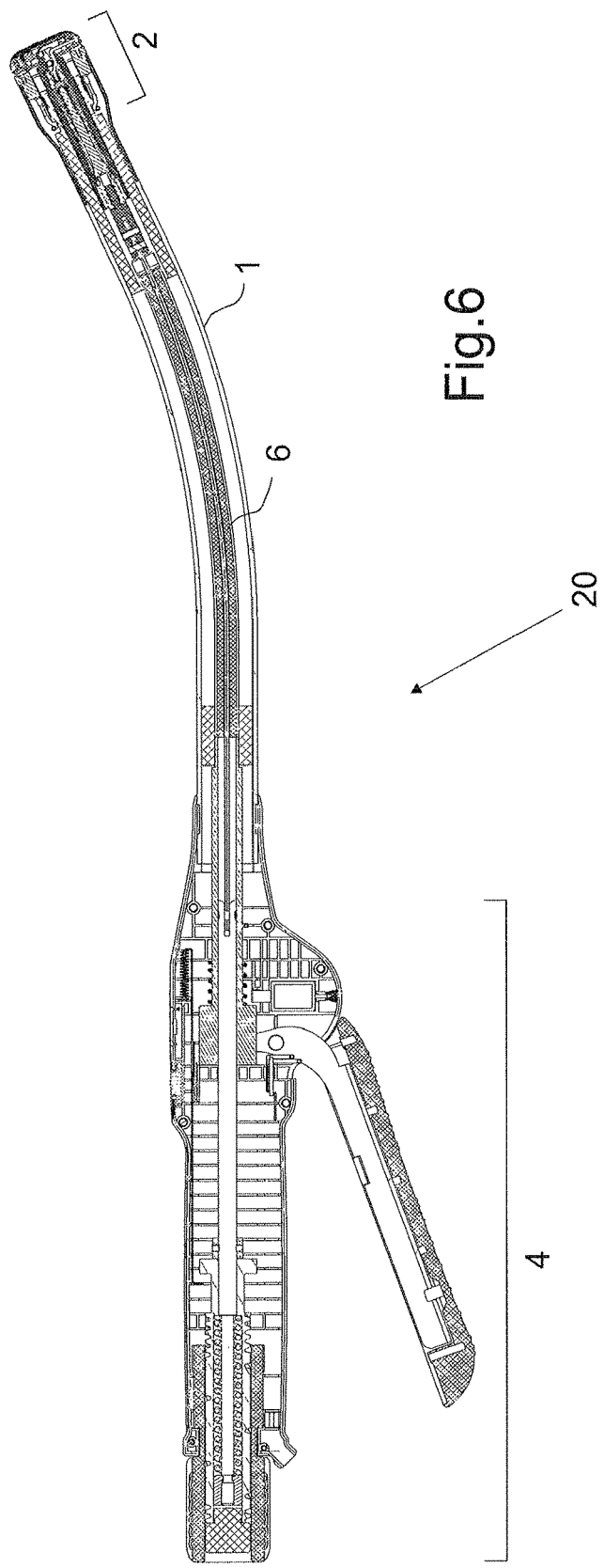
FIG. 6 is a schematic diagram of the electrosurgical instrument according to the first preferred exemplary embodiment of the present invention.

As can be taken from FIG. 1 in combination with FIGS. 5 and 6, a first exemplary embodiment of the present invention relates in particular to a circular electrosurgical (HF) instrument comprising a preferably curved instrument shaft 1 which has its distal end (facing the body) provided with a shaft head 2 and its proximal end (facing away from the body) provided with a handle or handle piece 4. Within the shaft 1, a push/pull profile element 6 is guided to be axially movable and has its distal end coupled to an axially acting circular cutting blade 8 which is supported in the shaft head 2 via a blade mount 10 so as to be axially shiftable. In the interior of the push/pull profile element 6, a push/pull shaft or rod, i.e. a push/pull unit preferably realized in the form of one or more sheet metal strips 12 is supported to be relatively movable, which has its distal end firmly coupled to a so-called trocar pin 14 which is supported within the blade mount 10 so as to be relatively shiftable therein and has its end inserted in an axial hollow shaft 16 of a distal anvil (electrode plate) 18. The anvil 18 forms a sort of plate or umbrella and has its one flat face arranged axially opposite the shaft head end face and can be axially moved via the pull/push rod 12 and the hollow shaft 16 relative to the shaft head 2. The end face of the shaft head 2 as well as the facing flat face of the anvil 18 are equipped with electrodes 17 associated to a bipolar HF current application means and connected to electric lines laid within the instrument shaft 1 and preferably within the push/pull profile element 6. Moreover, the anvil 18 and the shaft head 2 serve the purpose to axially and circularly clamp the body tissue between them and compress it with a predetermined pressure.

For the actuation/axial displacement of the anvil 18 with respect to the shaft head 2, the proximal end of the (circular) instrument which is illustrated as the first exemplary embodiment or of its handle piece 4 is provided with a rotary nut/hand wheel/rotary knob 20 which is supported to be rotatable around the longitudinal axis of the handle piece and provided with an internal thread which is in meshing engagement with an axially movable, but rotationally fixed hollow shaft/spindle 22 comprising an external thread; said hollow shaft/spindle, in turn, supports a pull/push rod 24 which is connected to the push/pull unit 12. Thus, rotating the rotary knob 20 causes a guided axial movement of the hollow shaft 22.

As can be taken in particular from FIG. 1, the hollow shaft 22 comprises an inner spring seat in the form of an inner ring shoulder 26 which is arranged on the distal end portion of the hollow shaft 22 and represents a sliding guide for the pull/push rod 12, 24. The pull/push rod 12, 24 has its proximal end provided with a spring seat in the form of an outer ring shoulder 28 which serves as a guide/slide bearing for an axially acting slideway of the push/pull rod 12, 24 within the hollow shaft 22. Inserted between the two spring seats is a compression spring/spiral spring 30 which surrounds the pull/push rod 12, 24 and transfers an axial movement of the hollow shaft 22 to the pull/push rod 12, 24.

Figure 2:
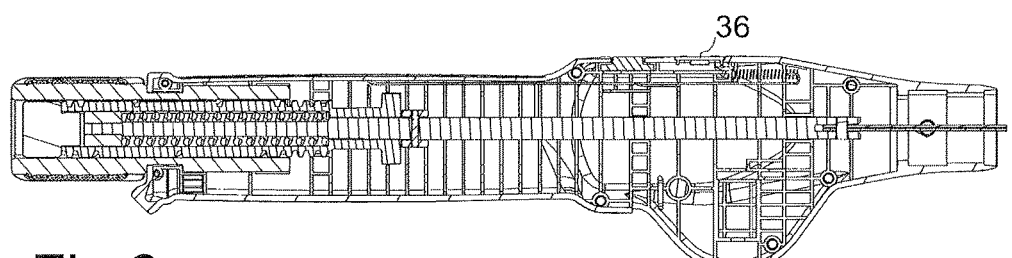
FIG. 2 is a longitudinal sectional view of a handle piece of the instrument according to FIG. 1 comprising an exemplary (visual) clamping pressure display installed therein and being in a (mechanical) operative connection with the mechanical pressure control means.
Figure 3:
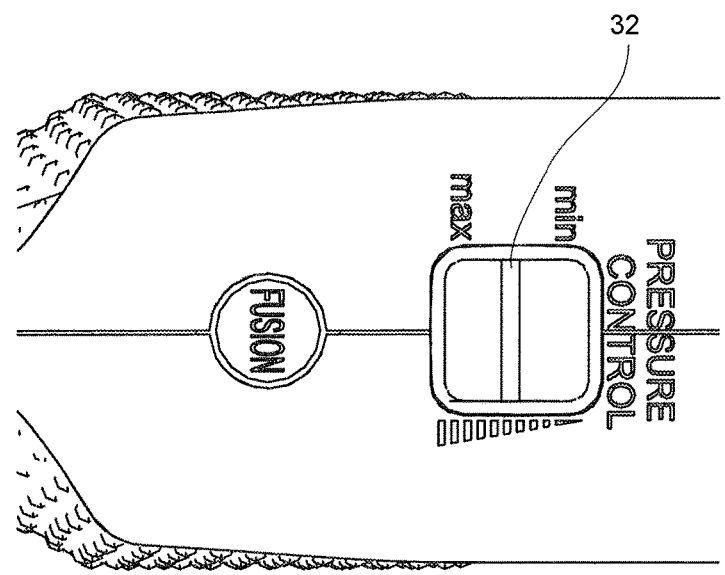
FIG. 3 shows an exemplary display scale of the display according to FIG. 2.

As can be taken from FIGS. 2 and 3, a display bar 32 is supported in the handle shell of the handle/handle piece 4 so as to be axially shiftable and comprises an engaging claw or hook 32a coming into engagement with an entraining protrusion 34 on the hollow shaft 22 whenever said hollow shaft has reached an axial position in the handle piece (handle shell) 4 in which the anvil 18 is about to rest against the end face of the shaft head 2 or is immediately in front of it (depending on the expectable tissue thickness of the body tissue to be clamped).

Figure 7:
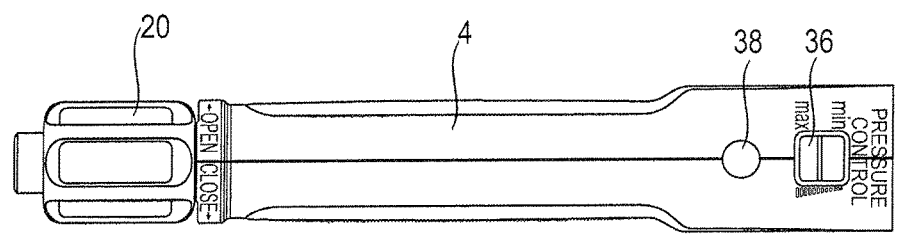
FIG. 7 is a top view of the instrument handle according to FIG. 4.

As far as to said axial position of the hollow shaft 22, the axial movement of the anvil 18 is performed via the pull/push rod 12 and the compression spring 30 still essentially without any force and without any compression of the compression spring 30. From said axial position, the anvil 18 does not move any more or only to a negligible extent depending on the compression of the clamped body tissue, so that a continued rotation of the rotary knob 20 (actuation mechanism) and the continued movement of the hollow shaft 22 caused thereby is compensated for substantially exclusively by a deformation of the compression spring 30. This deformation path is detected by a concomitant displacement of the display bar 32 and is displayed in a display window 36 according to FIG. 7.

Figure 11:
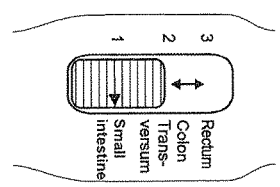
FIG. 11 is a schematic diagram of the adjustment device of a clamping pressure control device.

Said display window 36 preferably comprises two scale values, i.e. "min" and "max", between which the display bar 32 has to be situated in order to presuppose a sufficient spring deformation. As the spring pretensioning force is applied (in the presence of this spring deformation) via the one spring seat 28 to the pull/push rod 12, said force is transferred via the rod 12 to the anvil 18 which clamps the body tissue between itself and the shaft head 2 in a defined manner with a corresponding clamping pressure. Furthermore, the display window may be implemented as illustrated in FIG. 11. Here, the bar 32 would indicate that the right surface pressure for a specific tissue has been set.

At this moment, the electrodes 17 as well as the electric lines connected thereto can be acted upon with HF current via an HF trigger switch 38 (see in particular FIG. 4) at the handle piece 4. As soon as the application with electrical current has come to an end, a further scissors handle or handle bracket (manual lever) 40 supported on the handle piece 4 is operated, which is coupled to the push/pull profile element 6 in order to move the latter within the instrument shaft 1 and thus to advance the distal circular cutting blade 8 arranged thereon in axial direction toward the anvil 18. In doing so, said blade 8 severs any excess body tissue protruding radially inwards.

The advantage of the clamping pressure adjustment device according to the previous description of the first preferred exemplary embodiment of the invention may be summarized as follows:

If the anvil 18 is retracted together with the electrodes (plates) mounted thereon and rests against the instrument head 2 (or is shortly in front of it), the compression spring 30 begins to act between the hollow shaft 22 and the pull/push rod 12, 24. The user may now control the resultant surface pressure at the head via a defined spring travel. The user receives the direct feedback on its adjustment by the bar 32 which is preferably realized as a display sheet and entrained by the hollow shaft (hollow spindle) 22, with the option that the bar 32 may be equipped with a hand. The bar or the display sheet 32 is visible through the display window 36 in the handle 4 said window being arranged, in particular according to FIG. 7, preferably on the upper side of the handle and thus is readily readable in use. An additional display option may be realized via an end cap 42 of the pull/push rod 12, 24, said end cap gradually moving out of the distal end of the hollow shaft 22 with beginning deformation of the compression spring 30 (beginning relative movement between the hollow shaft 22 and the pull/push rod 12), thus becoming visible during adjusting the admissible range of the surface pressure.

Optionally, the handle shell may be provided with a stop 44 which comes to rest against the hollow shaft (hollow spindle) 22 at a certain axial position. In this embodiment, said stop 44 prevents that the allowable maximum admissible compression is exceeded.

The thread of the spindle 22 may also comprise zones of different pitches. By virtue of different pitches or corresponding gearing mechanisms, it is possible to create for instance a middle area with precise adjustment and a quick-adjustment area outside the presumably "ideal" compression. In other words, the hollow shaft 22 (hollow spindle) may comprise an area with large pitch for quickly moving the anvil 18, as long as the latter is close to the shaft head 2, and an area with small pitch for a slow deformation of the compression spring 30, if the anvil 18 rests against the shaft head 2 (or is closely in front of it).

Although not shown in detail, the operating principle of a triggering or displaying torque wrench may also be used instead of or in addition to the threaded spindle (hollow shaft) for realizing an adjustable surface pressure. In that case, the rotary knob would be coupled to the hollow spindle via a sliding clutch or any such trigger mechanism which upon exceeding the maximum admissible surface pressure would begin to slip and in this way prevent a further pressure build-up. An (additional) electronic evaluation of the surface pressure is also conceivable—for example with the aid of strain gauge strips on a torsion bar in the instrument—which may also be controlled in a motorized way, in particular with robot-assisted operation techniques such as in telesurgery.

Figure 8:
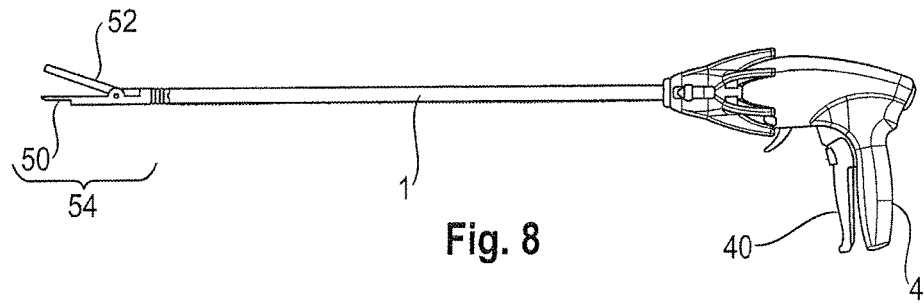
FIG. 8 is a side view of an electrosurgical instrument according to a second preferred exemplary embodiment of the present invention.
Figure 9:
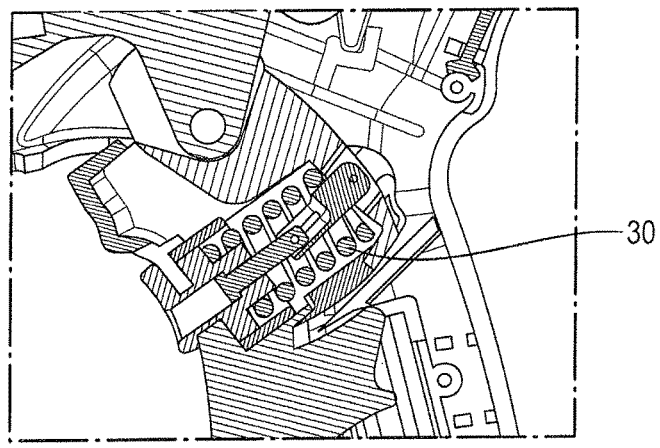
FIG. 9 is a side elevation of a handle piece of the second exemplary embodiment in the area of the clamping pressure control device.

FIGS. 8 and 9 show a second embodiment which is illustrated on the basis of a laparoscopic instrument with scissor- or forceps-like instrument branches at the shaft head; here, the compression spring 30 is situated in the movable lever 40 of the handle 4 which in this case for opening the forceps branches 50, 52 is coupled to the latter via a shaft gear train. Unlike the first embodiment, the instrument shown in FIG. 8 is not a circular sealing instrument, but a linear sealing instrument in which the electrodes are arranged along the forceps branches 50, 52.

Due to an adjustment feature on the lever 40, the user is able to vary the surface pressure acting between the clamping jaws 50, 52 in the distal jaw part 54. This allows the user to increase or reduce the surface pressure during use according to requirements or indication.

Specifically, the lever 40 according to FIG. 9 acts on the shaft gear train exclusively via the one tension/compression spring 30 which is compressed/deformed when the forceps branches 50, 52 rest against each other; in this process, the lever 40 will strike the instrument handle as from a defined swiveling angle, thus preventing a further swiveling motion and a further deformation of the spring 30. Here, the spring seat may be adjusted on the part of the lever 40 in order to bring about a larger or smaller spring deformation (pretensioning distance) within the scope of the maximum pivoting angle, making the maximum attainable spring force and hence the clamping pressure adjustable.

Figure 10:
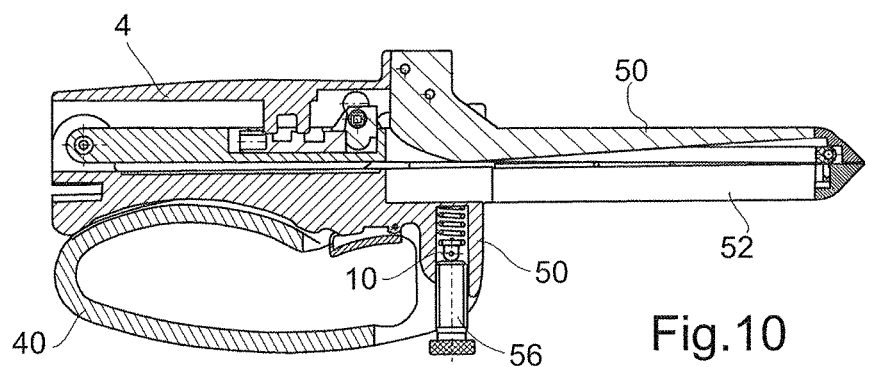
FIG. 10 is a longitudinal sectional view of an electrosurgical instrument of linear construction according to a third preferred exemplary embodiment of the invention.

FIG. 10 shows a third preferred exemplary embodiment of an electrosurgical instrument of the present invention in the form of a shaft-less linear sealing instrument comprising two linear forceps branches 50, 52 which are supported at their distal points immediately in an instrument handle 4 in the manner of pliers. The handle piece 4 has a lever or actuation bracket 40 pivotally articulated thereon which allows to open and close the forceps branches 50, 52. In this arrangement, the lever 40 acts exclusively via a compression spring 30 on the downstream actuation gear within the handle piece 4 for pivoting the forceps branches 50, 52, a lever-side spring seat being formed by a set screw screwed in the lever 40.

In this case, too, the maximum pivoting amount of the lever 40 is limited by a stop in the handle piece 4, correspondingly limiting the maximum spring pretensioning as of the moment when the forceps branches 50, 52 come to rest against each other. Adjusting the set screw 56 allows to adjust the value of the maximum attainable spring pretensioning within the maximum pivoting angle of the lever 40.

This means that in the linear sealing instrument according to FIG. 10, the compression spring 30 may be arranged in the center region of the instrument, here in front of the handle, i.e. on the actuation side of the lever 40. The maximum pivoting angle and thus the pretensioning of the spring 30 with already closed forceps branches 50, 52 can be adjusted by means of the position of a swiveling pin acting as a pivot bearing for the lever 40 on the handle shell 4. This circumstance controls the surface pressure acting in the closed state of the instrument. In this embodiment, the adjustment screw 56 illustrated as an adjustment feature adjusts the pretensioning of the spring 30 with closed forceps branches 50, 52.

Here, reference is made that also another adjustment principle such as an adjustment wedge comprising a downstream, axially movable spring seat bolt may be used instead of a set screw 56. In this case according to FIG. 11, the wedge would be shifted by means of a sliding key to which a display scale could be mounted at the same time, for instance for different body tissues.

This means that the possibility of adjusting the surface pressure is important with such linear sealing instruments, in particular with respect to the various indications and tissue types for which the instrument is used. In the following, some proposals for solution regarding said adjustment are set forth in more detail with respect to FIGS. 12a to 12c. It is to be noted that the person skilled in the art is able to transfer such proposals for solution both to linear and circular sealing instruments, which is why they are described here on the basis of a fundamental example which can be transferred to all embodiments explained above.

Figure 12A:
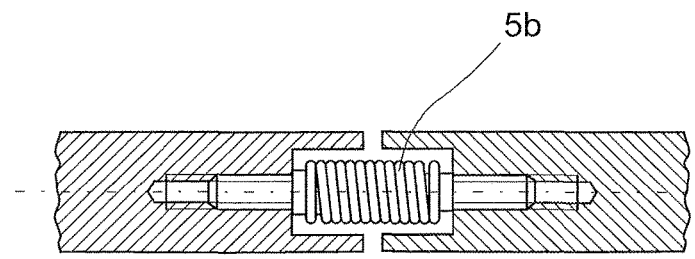
FIGS. 12a-12c show variants of the arrangement and the constructional implementation of a clamping pressure control device according to the invention on the basis of the first exemplary embodiment.

Instead of the compression spring of the first embodiment, it is also possible to install a disc spring stack, which can directly replace the compression spring, or a tension spring. FIG. 12a shows an example comprising a tension spring 5b which pulls the two parts of the sealing instrument toward each other, for example the hollow spindle and the pull/push rod supported therein. It is also possible to interpose the compression spring or the tension spring according to FIG. 12a at any place in the force gear train toward the one movable electrode branch.

Figure 12B:
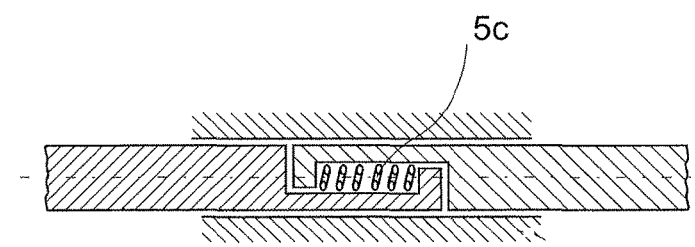

FIG. 12b shows a further alternative embodiment comprising a compression spring 5c which is interposed anywhere in the force gear train on the at least one electrode branch.

Figure 12C:
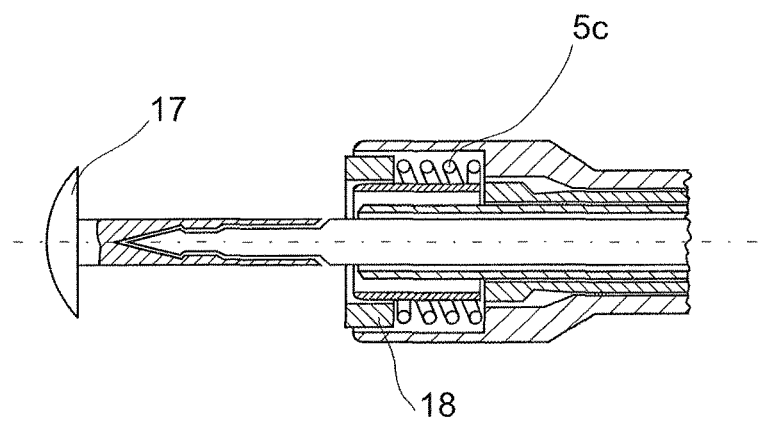
Figure 13:
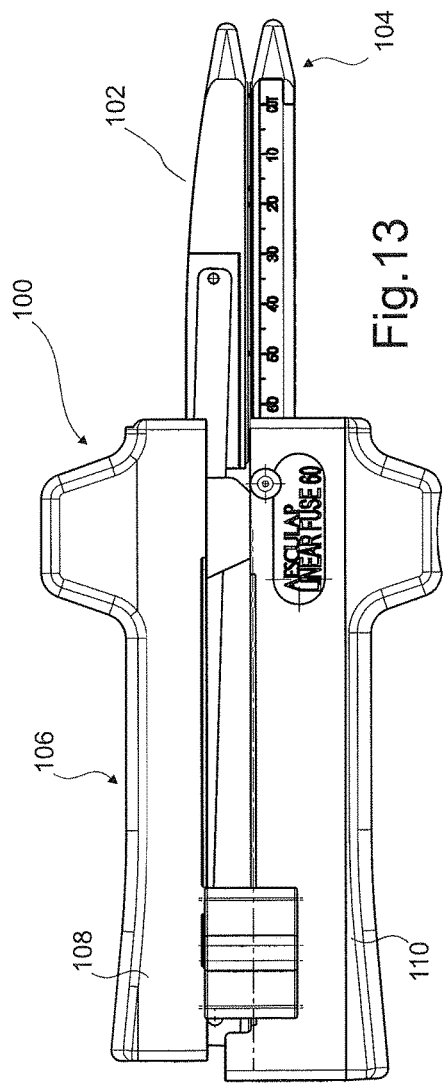
FIG. 13 is a longitudinal view of a further electrosurgical instrument of the linear type according to a fourth preferred exemplary embodiment of the invention.

FIG. 12c shows an embodiment using a compression spring 5c as in FIG. 12b. In this example, however, the compression spring is arranged in the instrument head of a circular electrosurgical instrument and thus acts directly on the instrument branch, now supported in the instrument head so as to be axially movable, as a spring-preloaded counter-bearing for the anvil.

By means of adjusting the mechanism (substantially consisting of nut, spindle and tension/compression spring as well as of the push/pull rod which is in operative connection with the spindle via the spring), it is possible as in the previously explained embodiments, in particular with circular sealing instruments, to apply a pretensioning force or clamping force depending on the thickness of the tissue. As an alternative to the threads described so far, corresponding pretensioning forces can also be applied in some other way, for instance via eccentric and adjustable clamping nubs. If a tissue is clamped which has a reduced thickness, the pretensioning force and/or the surface pressure in the tissue can be increased for instance by means of the forward feed or rotation of an eccentric cam exerting influence either on the spring pretensioning or the distance between the clamping jaws. Alternatively, the already explained screws may be used for this purpose. For somewhat thicker tissue types, however, turning back the eccentric cam allows to reduce the pretensioning force or surface pressure and hence to prevent a mechanic damage on the tissue due to compression.

As already explained above, the clamping pressure control device according to the invention may be installed in the instrument handle, for instance with shaft-type instruments comprising distal instrument branches or with linear, forceps-like instruments (without shaft) and interposed in the force transmission or moment transmission gear beginning here. As an alternative to this, it is also possible to integrate the clamping pressure control device in the area of the distal instrument head in case of shaft-type instruments (such as an anastomosis instrument) in the force transmission or moment transmission gear beginning there. To this end, the clamping control device may have its individual constructional design, in order to adapt to the spatial conditions and to correspondingly fit in the transmission gear components presently available.

FIGS. 13 to 16 show further alternative configurations for a clamping pressure control device according to the invention within the instrument handle on the basis of a linear instrument 100.

As is well known, a linear electrosurgical instrument 100 comprises two linear instrument branches 102, 104 which are articulated to each other within an instrument handle 106 preferably in the manner of a pair of scissors and are prolonged to form two handle levers 108, 10 in the zone proximal with respect to the hinge point. According to FIGS. 13 and 14, a transverse bolt 112 is formed on one of the handle levers 110 or one of the instrument branches 104 or is inserted therein; said transverse bolt can be engaged in clamping manner by a clamping pawl 114 which is articulated on the other handle lever 106, in order to apply a predetermined clamping force on the two instrument branches 102, 104 if the clamping pawl 114 and the transverse bolt 112 are fully latched/locked with each other according to FIG. 14. The predetermined clamping force thus depends on the position of the transverse bolt 112 relative to the clamping pawl 114 in the latched/locked state.

This offers the possibility, for instance, to insert the clamping pressure control device according to the invention exactly in this area of the force or moment transmission gear.

Figure 14:
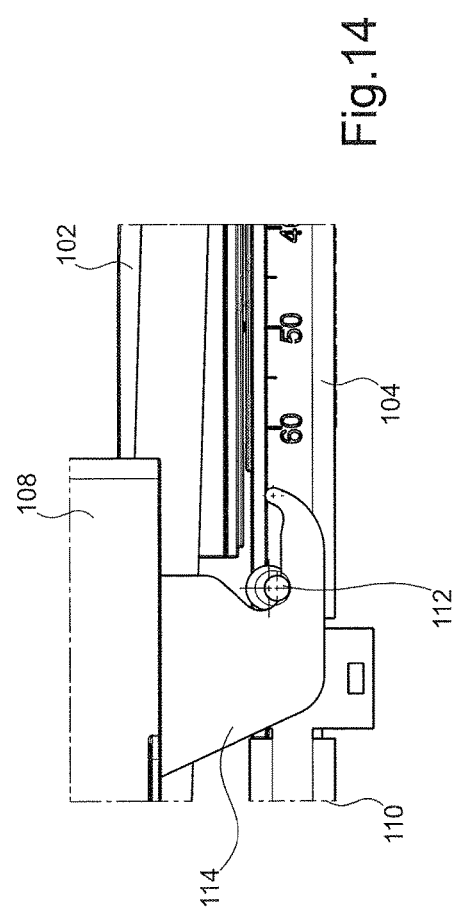
FIG. 14 is a longitudinal view of a tension mechanism of the electrosurgical instrument according to FIG. 13 in enlarged view.

According to FIG. 14, the transverse bolt 112 is realized as an eccentric cam which comes closer to or moves away from the clamping pawl 114 (and its engagement portion) if it is rotated. This allows to pre-adjust the clamping force between the instrument branches 102, 104 at the eccentric cam-transverse bolt 112 in the locked state of the clamping pawl 114 and in this way to adapt the instrument to different tissues.

Figure 15:
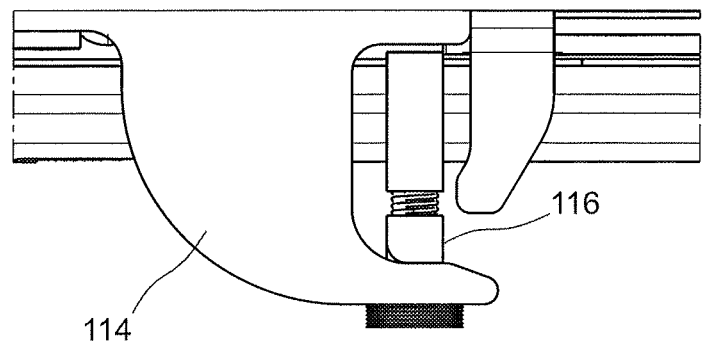
FIG. 15 is a longitudinal view of an alternative tension mechanism, with respect to FIG. 14, of the electrosurgical instrument according to FIG. 13.
Figure 16:
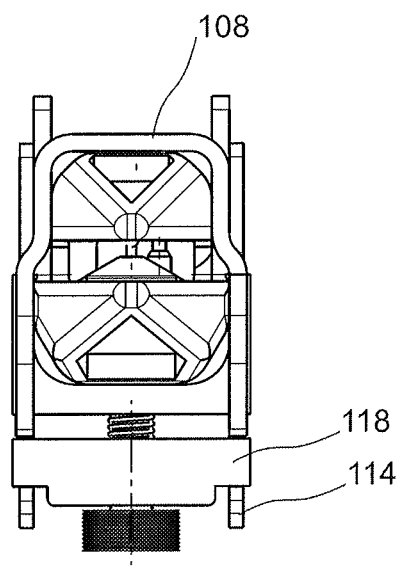
FIG. 16 is a rear view of the tension mechanism according to FIG. 15.

As an alternative to this, however, it is also possible to replace the above-mentioned transverse bolt 112 by a tensioning mechanism as it is indicated in FIGS. 15 and 16.

In this case, the one handle lever 108 also has a clamping pawl 114 mounted thereon which has its free pawl end provided with a formed-on engaging portion which can be brought into an interlocking engagement with a tension/compression screw 116. Said screw 116 is coupled to the other handle lever 110 or the instrument branch 104 connected to it, in order to apply a pressure force in the axial direction of the screw 116.

To this end, the screw 116 comprises a force introduction component (bar) 118 which can be made to engage the engagement portion of the clamping pawl 114 to apply the previously mentioned clamping force on the instrument branches 102, 104 according to the clamping pawl position. Said force introduction component 116 can be moved relative to the clamping pawl 114 upon turning the screw 116, in order to be able to (pre-)adjust the clamping force of the instrument branches in the locked clamping pawl position.

In both variants of the clamping pressure control device, the relative position between the clamping pawl and the transverse bolt/the force introduction component is adjustable, refraining from using a spring as the energy accumulator in this case. In this context, it is explicitly pointed out that the transverse bolt 112 or the force introduction component 118 may also be elastically supported to implement an energy accumulator in the sense of the preceding exemplary embodiments.

In order to avoid leakage, it is advantageous with the present invention and possibly important to detect the parameters acting on the tissue and to control them. Apart from the surface pressure whose control is effected by the previously described embodiments, these parameters also include the temperature, pressure, tissue impedance, distance of the electrodes and the position of the tissue in the body.

In the case of a circular sealing instrument for preparing an end-to-end-anastomosis as described above, it is a must to carry out several security-related steps in the correct order. In order to ensure that the user adheres to this correct sequence, it is possible to provide corresponding safety devices in the instrument in addition to the equipment for adjusting the surface pressure explained so far. Here, the following points would require attention:

It must not be allowed to be able to activate the HF current if the instrument is open.

It must not be allowed to be able to activate the HF current if the correct range of the surface pressure is not adjusted.

The cutting process must not be enabled unless the HF sealing has been carried out.

The safety precautions with usual circular clip suturing instruments such as explained above as prior art are of purely mechanical nature and may be overridden in case of mishandling. By way of example, setting clips and triggering the blade is possible without the anvil being set, if the trocar pin is completely retracted without the anvil being adapted.

The present embodiment is supposed to provide suitable safety precautions in particular for a circular sealing instrument according to the invention.

To this end, the interior of the distal instrument head is provided with a continuous axial contact bush 60 as shown in FIGS. 5 and 6, which is in contact with the HF actuation device 18 at the instrument handle 4 via electric lines and through which the trocar pin 14 can move in axial direction. Fixed on the trocar pin 14 is a further contact bush 62 which is electrically connected to the electrodes 17 on the anvil 18. The trocar pin 14 itself is made of an electrically non-conductive material (at least in parts). Said further contact bush 62 is positioned on the trocar pin 14 in axial direction such that it makes contact with the continuous contact bush 60 only if the anvil 18 is completely retracted toward the instrument head 2. If the trocar pin 14 is extended, there is no electrically conductive contact with the continuous contact bush 60. This ensures that the HF current cannot be activated if the instrument is open, as an error message appears otherwise.

Figure 4:
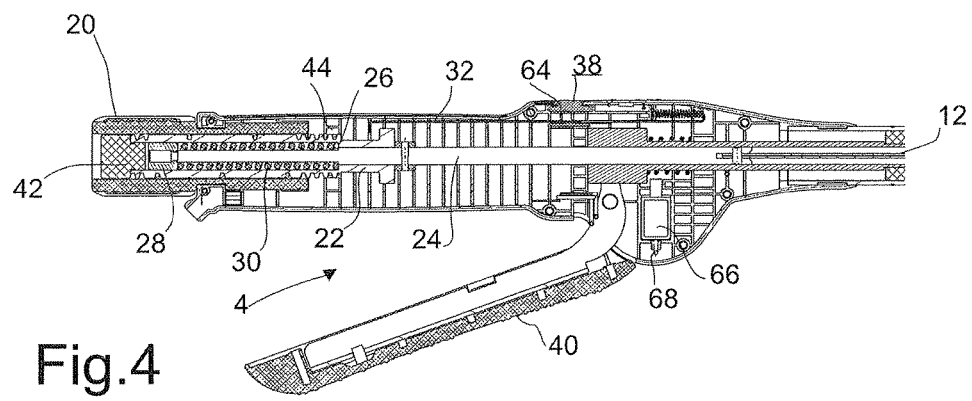
FIG. 4 shows an overall longitudinal section of the handle piece according to FIG. 3 including the manipulators for actuating the instrument head functions (effectors)

The proximal handle 4, illustrated in particular in FIG. 4, is provided with the manually operable HF trigger button (HF actuation device) 38 and a further check button 64. In the present case, the check button 64 is in operative connection with the display bar or display sheet metal 32 of the surface pressure display scale and is operated (by the bar) only if the correct range of the surface pressure has been set. If the actual value exceeds or falls below this range, the check button 32 will not be operated. This ensures that the HF trigger button 18 does not activate the HF current supply, if the wrong (or no) clamping pressure is set. Further, it is conceivable to highlight the correct range of the surface pressure with colors, e.g. red and green, or to visually highlight it in similar way.

Having correctly triggered the HF current, a lifting magnet 66 is (electrically) activated or retracted; arranged on said lifting magnet is a locking pin 68 which engages the moving mechanical system of the cutting blade actuation lever 40 and blocks it in the extended state. In the retracted state, however, the locking pin 68 unblocks the cutting operation if the sealing process effected by the HF current is completed. Optionally, in the event of a faulty energization (failure of the automatic drive system of the lifting magnet), there is the possibility to enable the cutting operation by a corresponding input at the generator (not illustrated).

A further safety means (not illustrated in the Figures) makes provision of a mechanical emergency actuation for the cutting blade, either bridging the lifting magnet or overcoming its lifting force. With this, security is provided against any faults of the generator and power blackouts. The mechanical emergency actuation has to be fastened to the instrument so as to be clearly visible and it must not be possible to actuate it unintentionally. This may be realized, for instance, by a sort of unlocking catch or a cover to be destroyed or removed deliberately.

The check button 64 for retrieving/detecting the correct surface pressure, which is coupled to the correct adjustment of the surface pressure as described above, represents a novel safety equipment for circular clip suturing instruments and/or circular sealing instruments but also for linear instruments. In combination with the lifting magnet 68 and the contacts in the instrument head 2 as described in the embodiment explained above, this concept offers higher safety to the user than a (currently known) clip suturing instrument. This results in a maximum level of monitoring and safety for the user and the patients with respect to the following three issues:

A query is made whether the instrument is closed.
A query is made whether the correct surface pressure has been adjusted.
It is not possible to effect the cut unless the sealing has been made.

Instead of the contact bushes, any electrical contacts may be used which serve the same purpose. This is also the case with the HF trigger button and the check button. The lifting magnet may be replaced by other electromechanic locking elements.

Although the safety means have been illustrated in the present embodiments by the example of instruments for HF sealing, it is also possible to use comparable devices which make sure that the cutting process occurs only after the sealing process, in principle also with clip suturing instruments or other instruments for producing anastomoses.

In summary, the present invention discloses mechanical systems for adjusting a surface pressure in particular for instruments for sealing tissue in anastomoses. The adjustability of the surface pressure, as described in the invention, may also be used for clip suturing instruments. It is particularly preferred that additional safety means are provided which prevent the anastomosis from being triggered if the instrument is not in a secured state in which the anastomosis is to be triggered.

The invention claimed is:
1. A surgical instrument comprising:
an actuation mechanism;
two tissue branches, at least one of the tissue branches being a movable tissue branch that is moveable relative to the other tissue branch and able to be applied to said other tissue branch with a predetermined or predeterminable contact pressure via the actuation mechanism while clamping body tissue between the tissue branches;
a handle; and
a clamping pressure controlling or adjustment device which is interconnected in a force or torque gear train in series between the actuation mechanism and the at least one movable tissue branch or within the actuation mechanism, the clamping pressure controlling or adjustment device comprising:
a first push/pull element and a second push/pull element that can be axially shifted relative to the first push/pull element, the first push/pull element and the second push/pull element being movable with respect to the handle; and
an energy accumulator provided serially between the first and second push/pull elements for transmitting an elastic force from the first push/pull element to the second push/pull element, the energy accumulator having a moving direction and a direction of elastic force transmission axially to the first push/pull element and/or to the second push/pull element,
the first and second push/pull elements being axially shiftable relative to each other to a non-actuated relative position in which the energy accumulator transmits no elastic force between the first and second push/pull elements, the non-actuated relative position being adjustable for adjusting and predetermining a maximum attainable contact pressure between the tissue branches.

2. The surgical instrument according to claim 1, wherein the clamping pressure controlling or adjustment device comprises an elastically yielding lifting cylinder with an elastic resilience that is adjustable in an axial direction.

3. The surgical instrument according to claim 1, comprising a force or torque gear train between the actuation mechanism and the tissue branches, wherein the energy accumulator can be loaded through the actuation mechanism by a defined/definable amount or which can be loaded within a defined/definable range of the amount, in which an actuation force or actuation moment resulting therefrom and transmitted by the force or torque gear train produces the predetermined or predeterminable contact pressure.

4. The surgical instrument according to claim 3, wherein the energy accumulator is a spring or spring arrangement which can be deformed according to the actuation force or actuation moment.

5. The surgical instrument according to claim 1, wherein the first and second push/pull elements which can be moved relative to each other are provided with seats, at least one of the seats being adjustable to produce different deformation paths of the energy accumulator within a maximum actuating travel or actuation amount of the actuation mechanism.

6. The surgical instrument according to claim 5 further comprising a display device, the display device comprising a drive bar which is operatively coupled to one of the seats, the drive bar entrained by said one of the seats when the energy accumulator begins to deform, thus calipering and displaying a deformation path.

7. The surgical instrument according to claim 1, wherein the actuation mechanism is a manual lever, a manually operable rotary knob or a motor-assisted drive system, which is in direct operative connection with the first push/ pull element of the clamping pressure controlling or adjustment device for the axial displacement thereof.

8. The surgical instrument according to claim 1, wherein the actuation mechanism is a manually operable rotary knob which is in direct operative connection with the first push/pull element of the clamping pressure controlling or adjustment device for the axial displacement thereof, the rotary knob being supported on an instrument case and, via an internal thread, is in engagement with the first push/pull element for its axial movement, said first push/pull element comprising a spindle body being in axial contact via the energy accumulator with the second push/pull element, the second push/pull element comprising a shaft being axially shiftable in the first push/pull element.

9. The surgical instrument according to claim 1, wherein the energy accumulator or the first push/pull element is mechanically coupled to a display device which is able to detect a loading amount caused by the actuation mechanism and display it as a current branch contact pressure in a visual manner.

10. The surgical instrument according to claim 1, further comprising a stop for limiting a maximum actuating travel of the actuation mechanism.

11. The surgical instrument according to claim 1, further comprising a sliding clutch which is arranged between the actuation mechanism and the energy accumulator and acts as a force or torque limiter.

12. The surgical instrument according to claim 1, wherein the first push/pull element comprises a hollow shaft and the second push/pull element is slidingly arranged within the first push/pull element.

13. The surgical instrument according to claim 12, wherein the energy accumulator is arranged inside the hollow shaft, and the hollow shaft comprises an inner seat in the form of an inner ring shoulder which forms a support surface for a first end of the energy accumulator and forms a sliding guide for the second push/pull element.

14. The surgical instrument according to claim 13, wherein the second push/pull element has an end provided with an outer seat in the form of an outer ring shoulder, the outer ring shoulder forming a support surface for a second end of the energy accumulator opposite the first end, the outer ring shoulder also forming a slide bearing for an axially acting slideway of the second push/pull element within the hollow shaft.

15. The surgical instrument according to claim 14, wherein the energy accumulator is inserted between the inner seat and outer seat and surrounds the second push/pull element so that the energy accumulator transfers an axial movement and an axial force of the first push/pull element to the second push/pull element.

16. The surgical instrument according to claim 1, wherein the surgical instrument is in an HF-design.

17. The surgical instrument according to claim 1, wherein the first push/pull element, the energy accumulator and the second push/pull element are aligned coaxially to each other.

* * * * *